(12) United States Patent
Ierulli

(10) Patent No.: US 10,893,971 B2
(45) Date of Patent: Jan. 19, 2021

(54) EXTERNAL NASAL DILATOR WITH MULTIPLE DISCRETE DILATION POINTS

(71) Applicant: Joseph V. Ierulli, Bradenton, FL (US)

(72) Inventor: Joseph V. Ierulli, Bradenton, FL (US)

(73) Assignee: Corbett Lair, Inc., Sarasota, FL (US)

( * ) Notice: Subject to any disclaimer, the term of this patent is extended or adjusted under 35 U.S.C. 154(b) by 106 days.

(21) Appl. No.: 16/167,441

(22) Filed: Oct. 22, 2018

(65) Prior Publication Data

US 2020/0121488 A1    Apr. 23, 2020

(51) Int. Cl.
A61F 5/08    (2006.01)
A61M 29/00    (2006.01)

(52) U.S. Cl.
CPC .............. *A61F 5/08* (2013.01); *A61M 29/00* (2013.01); *A61M 2210/0618* (2013.01)

(58) Field of Classification Search
CPC .. A61F 5/56; A61F 2005/0197; A61F 13/126; A61F 5/08; A61F 2/0063; A61F 2002/0068; A61B 17/085
See application file for complete search history.

(56) References Cited

U.S. PATENT DOCUMENTS

| | | | |
|---|---|---|---|
| 5,476,091 A | 12/1995 | Johnson |
| 5,479,944 A | 1/1996 | Petruson |
| 5,533,499 A | 7/1996 | Johnson |
| 5,533,503 A | 7/1996 | Doubek et al. |
| 5,546,929 A | 8/1996 | Muchin |
| 5,549,103 A | 8/1996 | Johnson |
| RE35,408 E | 12/1996 | Petruson |
| 5,611,333 A | 3/1997 | Johnson |
| 5,653,224 A | 8/1997 | Johnson |
| 5,706,800 A | 1/1998 | Cronk et al. |
| 5,718,224 A | 2/1998 | Muchin |
| 5,769,089 A | 6/1998 | Hand et al. |
| 5,890,486 A | 4/1999 | Mitra et al. |
| 5,931,854 A | 8/1999 | Dillon |
| 5,957,126 A | 9/1999 | Neeser |
| 6,006,746 A | 12/1999 | Karell |
| 6,029,658 A | 2/2000 | De Voss |
| 6,058,931 A | 5/2000 | Muchin |
| 6,065,470 A | 5/2000 | Van Cromvoirt et al. |
| 6,098,616 A | 8/2000 | Lundy et al. |
| 6,196,228 B1 | 3/2001 | Kreitzer et al. |
| 6,244,265 B1 | 6/2001 | Cronk et al. |
| 6,276,360 B1 | 8/2001 | Cronk et al. |
| 6,318,362 B1 | 11/2001 | Johnson |

(Continued)

FOREIGN PATENT DOCUMENTS

EP    855175 A1    7/1998
ES    289561    10/1985

*Primary Examiner* — Alexander J Orkin
(74) *Attorney, Agent, or Firm* — Mersenne Law

(57) ABSTRACT

An external nasal dilator comprises resilient and engagement elements, and includes end regions adapted to engage tissues overlaying and adjacent first and second nasal passages of a human nose. Each end region includes a plurality of resilient spring finger components separated therebetween by engagement element tab extensions. The end regions are further adapted to extend around the anatomical depression formed by the alar crease adjacent each nostril. When in use the dilator stabilizes or expands said tissues and prevents or inhibits the nasal outer walls from drawing inward during breathing.

11 Claims, 13 Drawing Sheets

(56) References Cited

U.S. PATENT DOCUMENTS

| | | | |
|---|---|---|---|
| 6,352,548 B1 * | 3/2002 | Blach | A61D 7/04 128/200.24 |
| 6,357,436 B1 | 3/2002 | Kreitzer et al. | |
| 6,375,667 B1 | 4/2002 | Ruch | |
| 6,453,901 B1 | 9/2002 | Ierulli | |
| 6,470,883 B1 | 10/2002 | Beaudry | |
| 6,550,474 B1 | 4/2003 | Anderson et al. | |
| 6,694,970 B2 | 2/2004 | Spinelli et al. | |
| 6,769,428 B2 | 8/2004 | Cronk et al. | |
| 6,769,429 B1 | 8/2004 | Benetti | |
| 7,067,710 B1 | 6/2006 | Beaudry | |
| 7,114,495 B2 | 10/2006 | Lockwood, Jr. | |
| D639,762 S | 6/2011 | Brogden et al. | |
| D644,325 S | 8/2011 | Brunner et al. | |
| D644,324 S | 10/2011 | Brunner et al. | |
| 8,047,201 B2 | 11/2011 | Guyuron et al. | |
| 8,062,329 B2 | 11/2011 | Ierulli | |
| D651,710 S | 1/2012 | Brogden et al. | |
| 8,115,049 B2 | 2/2012 | Beaudry | |
| D659,245 S | 5/2012 | Ierulli | |
| 8,188,330 B2 | 5/2012 | Beaudry | |
| D662,203 S | 6/2012 | Smith | |
| D667,543 S | 9/2012 | Ierulli | |
| D671,643 S | 11/2012 | Ierulli | |
| D672,461 S | 12/2012 | Brogden et al. | |
| D672,872 S | 12/2012 | Brunner et al. | |
| D673,270 S | 12/2012 | Brunner et al. | |
| 8,342,173 B2 | 1/2013 | Lockwood, Jr. | |
| 8,444,670 B2 | 5/2013 | Ierulli | |
| 8,584,671 B2 | 11/2013 | Ierulli | |
| 8,616,198 B2 | 12/2013 | Guyuron et al. | |
| 8,617,199 B2 | 12/2013 | Eull et al. | |
| 8,641,852 B2 | 2/2014 | Ierulli | |
| D707,814 S | 6/2014 | Ierulli | |
| D707,815 S | 6/2014 | Ierulli | |
| 8,834,511 B2 | 9/2014 | Holmes et al. | |
| 8,834,512 B1 | 9/2014 | Brown et al. | |
| 8,834,514 B2 | 9/2014 | Smith | |
| 8,858,587 B2 | 10/2014 | Ierulli | |
| D722,161 S | 2/2015 | Reyers | |
| D722,162 S | 2/2015 | Reyers | |
| D725,772 S | 3/2015 | Ierulli | |
| D725,773 S | 3/2015 | Ierulli | |
| 9,095,422 B2 | 8/2015 | Gray | |
| D738,496 S | 9/2015 | Peck | |
| D739,015 S | 9/2015 | Martin | |
| 9,119,620 B2 | 9/2015 | Peterson et al. | |
| D741,997 S | 10/2015 | Ierulli | |
| D741,998 S | 10/2015 | Martin | |
| D743,544 S | 11/2015 | Ierulli | |
| D743,545 S | 11/2015 | Ierulli | |
| D743,565 S | 11/2015 | Engel et al. | |
| D745,147 S | 12/2015 | Ierulli | |
| 9,204,988 B1 | 12/2015 | Fischell | |
| D746,982 S | 1/2016 | Ierulli | |
| D747,478 S | 1/2016 | Brunner et al. | |
| D753,294 S | 4/2016 | Guyuron et al. | |
| D755,376 S | 5/2016 | Ierulli | |
| D758,575 S | 6/2016 | Ierulli | |
| D758,576 S | 6/2016 | Ierulli et al. | |
| D759,240 S | 6/2016 | Ierulli | |
| D759,241 S | 6/2016 | Ierulli | |
| D759,242 S | 6/2016 | Ierulli | |
| 9,364,367 B2 | 6/2016 | Ierulli | |
| 9,364,368 B2 | 6/2016 | Ierulli | |
| 9,381,332 B2 | 7/2016 | Judd | |
| D764,055 S | 8/2016 | Ierulli et al. | |
| D764,662 S | 8/2016 | Ierulli et al. | |
| 9,414,957 B1 | 8/2016 | Fischell | |
| 9,427,945 B2 | 8/2016 | Gray et al. | |
| D779,666 S | 2/2017 | Ierulli et al. | |
| D779,667 S | 2/2017 | Ierulli et al. | |
| 9,566,183 B1 | 2/2017 | Fischell | |
| D788,298 S | 5/2017 | Guyuron | |
| 9,642,995 B2 | 5/2017 | Fenton et al. | |
| D789,531 S | 6/2017 | Ierulli | |
| D790,058 S | 6/2017 | Ierulli et al. | |
| D790,695 S | 6/2017 | Ierulli | |
| D791,312 S | 7/2017 | Peck | |
| D791,314 S | 7/2017 | Ierulli | |
| 9,730,827 B2 | 8/2017 | Ierulli | |
| 9,730,828 B2 | 8/2017 | Ierulli | |
| 9,775,738 B2 | 10/2017 | Andre | |
| 9,844,456 B2 | 12/2017 | Ierulli | |
| 9,901,479 B2 | 2/2018 | Holmes | |
| 9,901,480 B2 | 2/2018 | Ierulli | |
| 9,901,481 B2 | 2/2018 | Ierulli | |
| D812,749 S | 3/2018 | Ierulli | |
| D813,387 S | 3/2018 | Ierulli et al. | |
| D814,029 S | 3/2018 | Ierulli | |
| 10,010,442 B2 | 7/2018 | Ierulli | |
| 2008/0058858 A1 | 3/2008 | Smith | |
| 2008/0097517 A1 | 4/2008 | Holmes et al. | |
| 2009/0125052 A1 | 5/2009 | Pinna et al. | |
| 2009/0234383 A1 | 9/2009 | Ierulli | |
| 2010/0210988 A1 | 8/2010 | Dallison | |
| 2010/0298861 A1 | 11/2010 | Fenton | |
| 2011/0000483 A1 | 1/2011 | Matthias et al. | |
| 2011/0054517 A1 | 3/2011 | Holmes et al. | |
| 2011/0166594 A1 | 7/2011 | Eull | |
| 2011/0224717 A1 | 9/2011 | Lockwood | |
| 2012/0004683 A1 | 1/2012 | Gray | |
| 2012/0022582 A1 | 1/2012 | Guyuron | |
| 2012/0067345 A1 | 3/2012 | Shilon | |
| 2012/0172923 A1 | 7/2012 | Fenton | |
| 2012/0209313 A1 | 8/2012 | Ierulli | |
| 2012/0232455 A1 | 9/2012 | Beaudry | |
| 2013/0104882 A1 | 5/2013 | Ierulli | |
| 2013/0118488 A1 | 5/2013 | Ledogar | |
| 2014/0194922 A1 | 7/2014 | Ierulli | |
| 2014/0148844 A1 | 10/2014 | Andre | |
| 2014/0296904 A1 | 10/2014 | Andre | |
| 2014/0350596 A1 | 11/2014 | Smith | |
| 2015/0005812 A1 | 1/2015 | Holmes | |
| 2015/0012035 A1 | 1/2015 | Ierulli | |
| 2015/0051636 A1 | 2/2015 | Lockwood | |
| 2015/0090398 A1 | 4/2015 | Ierulli | |
| 2015/0090399 A1 | 4/2015 | Ierulli | |
| 2015/0094757 A1 | 4/2015 | Ierulli | |
| 2015/0094758 A1 | 4/2015 | Ierulli | |
| 2015/0216709 A1 | 8/2015 | Peck | |
| 2015/0230966 A1 | 8/2015 | Ierulli | |
| 2015/0250637 A1 | 9/2015 | Ierulli | |
| 2015/0290021 A1 | 10/2015 | Gray | |
| 2015/0359654 A1 | 12/2015 | Bentivegna et al. | |
| 2016/0008161 A1 | 1/2016 | Ierulli et al. | |
| 2016/0278967 A1 | 9/2016 | Ierulli | |
| 2016/0278968 A1 | 9/2016 | Ierulli | |
| 2016/0339619 A1 | 11/2016 | Gray et al. | |
| 2017/0112653 A9 | 4/2017 | Ierulli | |
| 2017/0143531 A9 | 5/2017 | Ierulli | |
| 2017/0151084 A9 | 6/2017 | Ierulli | |
| 2018/0021163 A9 | 1/2018 | Ierulli | |
| 2018/0028346 A1 | 2/2018 | Ierulli | |
| 2018/0071131 A1 | 3/2018 | Ierulli | |

* cited by examiner

FIG. 19 PRIOR ART
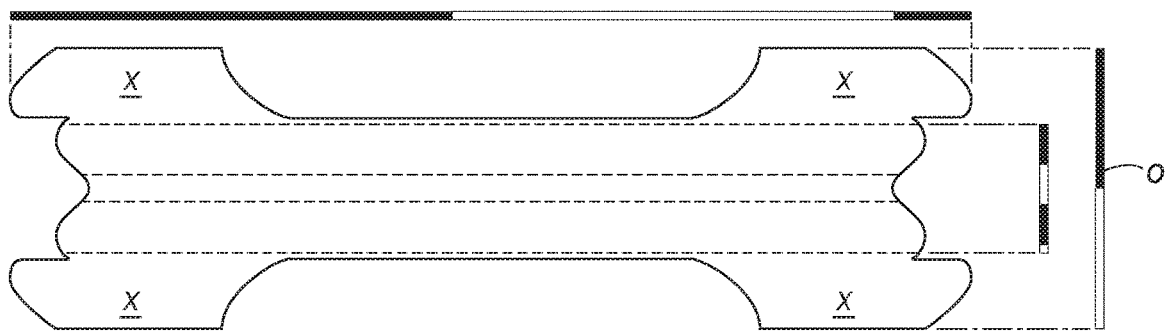
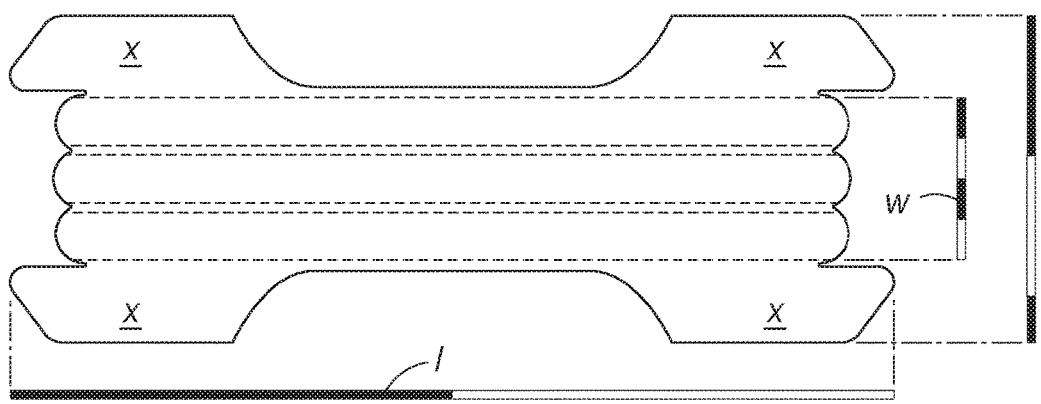
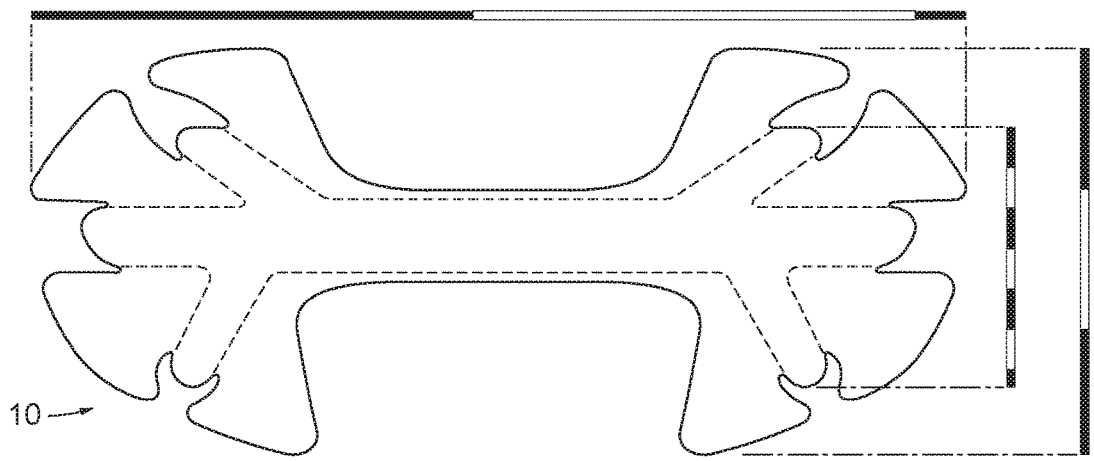
FIG. 20

|  | *l* | *o* | *w* |
|---|---|---|---|
| PRIOR ART TWO-BAND | *l* + 8.7% | *o* = 1.0 | *w* −20% |
| PRIOR ART THREE-BAND | *l* = 1.0 | *o* + 17% | *w* = 1.0 |
| DILATOR 10, FIG. 20 | *l* + 5.8% | *o* + 45% | *w* + 61% |
| DILATOR 10, FIG. 21 | *l* + 4.6% | *o* + 73% | *w* + 110% |
| DILATOR 10, FIG. 22 | *l* + 4.6% | *o* + 62% | *w* + 92% |
*Fig. 23*
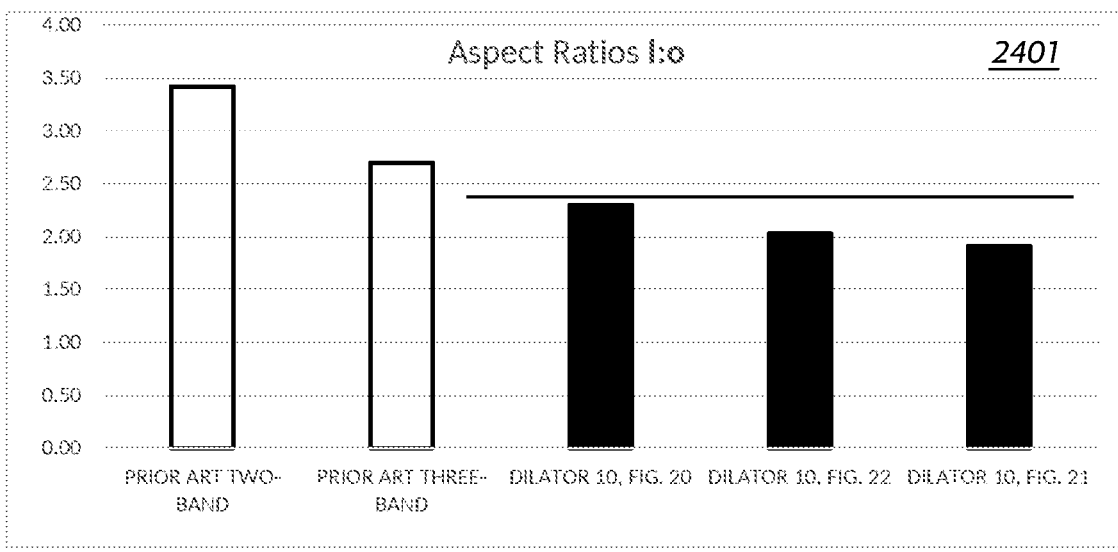
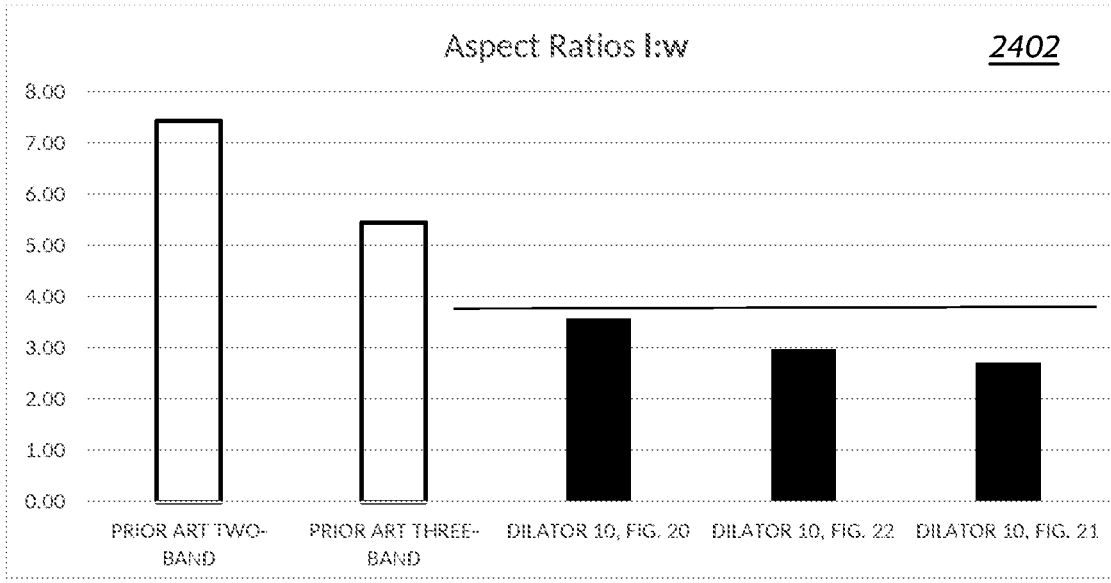
*Fig. 24*

EXTERNAL NASAL DILATOR WITH MULTIPLE DISCRETE DILATION POINTS

CONTINUITY AND CLAIM OF PRIORITY

This is an original U.S. patent application.

FIELD

The present invention relates generally to medical devices, and more particularly to apparatus for and methods of supporting and stabilizing or dilating external tissue in humans. As disclosed and taught in the preferred embodiments, the tissue dilator devices are particularly suitable for, and are directed primarily to, external nasal dilators for supporting, stabilizing, and dilating nasal outer wall tissues adjacent and overlying nasal airway passages of the human nose. The United States Food and Drug Administration classifies the external nasal dilator as a 510(K) Exempt [Medical] Device Class r, product code LWF, regulation No. 874,3900.

BACKGROUND

External nasal dilators (END) are well disclosed in the art and are widely available in the retail consumer markets where they are generally referred to as nasal strips or nasal dilator strips. In use the END extends over the skin surfaces of the nose, flexed across the bridge thereof and adhered to the skin surface of the nasal passage outer wall tissues on each side of the bridge.

The functional part of the END is at least one resilient member (synonymously referred to in the art as a spring, spring member, resilient band, resilient member band, spring band, or bridge) that extends along the length of the nasal dilator. When flexed, the resilient member exerts spring biasing forces that, when engaged to the nose, urge the nasal passage outer wall tissues outward, stabilizing the outer walls and expanding, or dilating, the nasal passages underneath.

Stabilized nasal outer walls and/or dilated nasal passages may beneficially affect nasal obstruction and nasal congestion by reducing nasal airflow resistance. Stabilized nasal outer walls inhibit collapse of the outer wall tissues during inhalation. Dilated nasal passages increase cross sectional area and nasal cavity volume. Stabilization and/or dilation, particularly at the nasal valve, results in a corresponding improvement in nasal breathing patency. Improved nasal patency may have beneficial effects generally, may increase oxygen uptake, may improve sleep, may reduce sleep disturbances, or may improve nasal snoring or obstructive sleep apnea (OSA). External nasal dilators have been shown to have beneficial effects for athletes, particularly in sports where a mouth-guard is worn.

SUMMARY

Nasal dilators of the present invention are capable of flexing in a direction oblique or perpendicular to a surface place thereof, such that the dilator returns to a substantially planar or pre-flexed state when released from flexure. In use the dilator stabilizes portions of the tissues extending along and adjacent the nasal passages and prevents, or at least inhibits, the tissues from drawing inward during breathing, particularly at the nasal valve. The dilator expands, or dilates, the nasal passages. The nasal dilator adheres comfortably to skin surface of the nose and is easily removed with little or no stress thereto.

Nasal dilators of the present invention use spring finger components extending outward from a resilient member mid-section component to engage multiple discrete dilation points overlaid or adjacent along the first and second nasal passages. Resiliency, or spring biasing forces, generated by the nasal dilator is distributed from the resilient member mid-section to the spring fingers, and by extension, to the multiple discrete dilation points: upper spring fingers extend up and away from the nasal valve area; middle spring fingers extend substantially over and in line with the nasal valve; lower spring fingers extend away and downward from the nasal valve area to the nasal vestibule area toward the nostril opening.

By directing total spring biasing forces in this manner, stabilization and/or dilation is directed to a greater portion of the nasal passages compared to a nasal dilator in which a substantially rectangular resilient member(s) overlays only the tissues directly over the nasal valve. The nasal dilator resilient element may be longitudinally separated into two or three individual resilient members, or a single resilient member may be slotted to form from three to six resilient branches extending horizontally outward from near the center of the mid-section. Additionally, first and second end regions of the nasal dilator are configured to extend around the curvature of the nostril so as to avoid spanning the anatomical depression formed by the alar crease of the nose.

Nasal dilators of the present invention have separate resilient and engagement elements combined into a single body truss. The engagement element functions primarily to affix, adhere, or engage the dilator to the skin surfaces of the nose. The engagement element, by itself, provides little or no nasal dilation (although depending on the material used, could provide some stabilization to the nasal passage outer walls). The resilient element, by itself and flexed across the bridge of the nose, generally will not remain well-engaged thereto. Thus, nasal dilators of the present invention preferably comprise both resilient and engagement elements.

The nasal dilator, formed as a single body truss, comprises a laminate of vertically stacked material layers, including: a base layer comprising at least one base member, a resilient layer comprising at least one resilient member, and a cover layer comprising at least one cover member. The base and cover layers, either separately or combined, together with a biocompatible adhesive disposed thereon for engaging the skin, provide the primary engagement element of the nasal dilator. Where the base layer has significantly less surface area than the cover layer, adhesive on the skin-engaging side of the base layer may be optionally eliminated. With or without adhesive, the base layer may also serve as a compressible buffer between the nasal dilator and the skin engaged thereby, as has been historically common in medical devices which remain in contact with the skin for any length of time. The resilient layer may optionally adhesively engage the skin directly.

Dilator layers may be secured to each other by any suitable means such as stitching or fastening, heat or pressure bonding, ultrasonic welding, or the like, but are preferably laminated by an adhesive substance disposed on at least one flat surface side of at least one layer. At least a portion of one flat surface of the base or cover layer is preferably laminated to one of two flat surfaces of the resilient layer.

TERMINOLOGY AND ILLUSTRATION NOTES

The terms spring biasing, spring biasing force, spring force, resiliency, spring constant, etc. as used herein are generally synonymous. Nasal dilators of the present invention may generate spring biasing force in a range of from about 15 grams to about 60 grams. A preferred range is from about 15 grams to about 35 grams for non-athletes, and from about 25 grams to about 45 grams for use in training, conditioning and competition by athletes. Less than 15 grams of spring biasing may not provide enough stabilization or dilation for some users, while greater than 35 grams may be uncomfortable for non-athletic use, such as during sleep, work or study.

The nasal dilator resilient member is semi-rigid; it is flexible out-of-plane with very little or no in-plane elongation. Strictly speaking, the term resilient may be used to describe objects that exhibit either 'flexure' or 'elasticity'. For purposes of the present invention, however, the terms resilient, resiliency, spring biasing, etc., mean flexure out-of-plane, in a direction perpendicular or oblique to the surface plane, while being substantially rigid in-plane. This is different from, for example, an elastic web that stretches in a direction parallel to its surface plane, even though both the elastic web and the nasal dilator resilient member may return at least substantially to their initial positions after stretch or flexure, respectively. Nasal dilators herein may be described as "capable of flexing" (when the dilator is in an initial or un-flexed position), or "flexed" (when the dilator is engaged to the nose of a user).

The present invention is not limited to the illustrated or described embodiments, which are examples of forms of the present invention. All structures and methods that embody similar functionality are intended to be covered hereby. The nasal dilators depicted, taught, enabled and disclosed herein represent new, useful and non-obvious nasal dilator devices having a variety of alternative embodiments. Some embodiments of the present invention may refer to, or cross reference, other embodiments. It may be apparent to one of ordinary skill in the art that nasal dilator features, construction or configuration may be applied, interchanged or combined between and among the preferred embodiments.

For descriptive clarity, certain terms may be used in the specification and claims: Vertical refers to a direction parallel to thickness, such as the thickness of a finished article, a member or component, or a laminate. Horizontal refers to length or longitudinal extent, such as that of a finished article or element thereof, or a direction parallel thereto. Lateral refers to its width or lateral extent. Longitudinal also refers to length, perpendicular to width or lateral extent. A longitudinal centerline is consistent with the long axis of a finished device, element, member or layer, bisecting its width midway between the long edges. A lateral centerline bisects the long axis midway along its length, perpendicular to the longitudinal centerline. The terms upper and lower refer to object orientation, particularly in plan views, relative to the top and bottom of the drawing sheet.

Broken lines and dashed lines may be used in the drawings to aid in describing relationships or circumstances with regard to objects:

A broken line including a dash followed by three short spaces with two short dashes therebetween indicates separation for illustrative purposes, such as in an exploded view, or to indicate an object or objects removed or separated from one or more other objects, primarily for illustrative clarity.

A dashed line (sometimes referred to as a shadow line) of successive short dashes with short spaces therebetween may be used to illustrate an object or element generically, to illustrate one object underneath another, or to reference environment such as facial features; or for clarity, to show location, such as the space an object or structure will occupy, would occupy, did occupy or may occupy; or for illustrative purposes, to represent an object, structure, element or layer(s) as transparent so that other objects more pertinent to the discussion at hand may be highlighted or more clearly seen.

A broken line including a long dash followed by a short space, a short dash and another short space is used to call out a centerline or an angle, or to indicate alignment; when accompanied by a bracket, to call out a section, segment or portion of an object or a group of objects; to illustrate a spatial relationship between one or more objects or groups of objects, or to create separation between objects for the purpose of illustrative clarity.

In the drawings accompanying this disclosure like objects are generally referred to with common reference numerals or characters, except where variations of otherwise like objects must be distinguished from one another. Where there is a plurality of like objects in a single drawing figure corresponding to the same reference numeral or character, only a portion of said like objects may be identified. After initial description in the text, some reference characters may be placed in a subsequent drawing(s) in anticipation of a need to call repeated attention to the referenced object. Where a feature or element has been previously described, shadow lines, or dashed lines, may be used to generically illustrate the feature or element together with a generic reference character. Drawings are rendered to scale—particularly plan views—but may be enlarged from actual size for illustrative clarity. Similarly, thickness may be slightly exaggerated for illustrative clarity.

BRIEF DESCRIPTION OF DRAWINGS

FIG. 19 shows plan views of prior art nasal dilators.

FIG. 20 is a plan view of the nasal dilator of FIG. 1.

FIG. 23 is a table that originally appeared in the Specification at [0065].

FIG. 24 shows two related graphs that originally appeared in the Specification at [0068] and [0069].

DETAILED DESCRIPTION

Embodiments of a nasal dilator, 10, in accordance with the present invention are illustrated in FIGS. 1-8, 10, 12-18 and 20-22.

Figure 1:
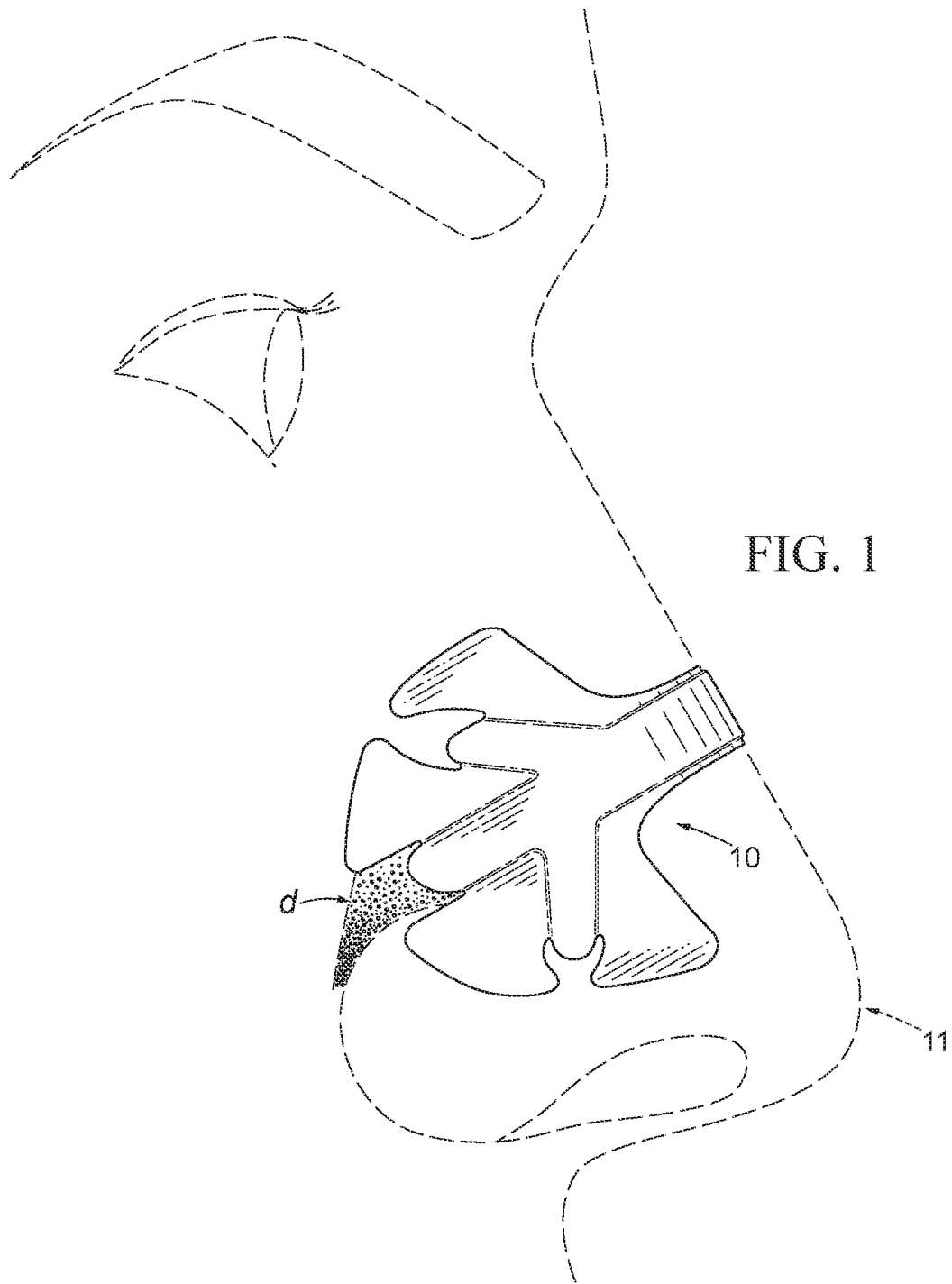
FIG. 1 is a perspective view of a nasal dilator in accordance with the present invention flexed across a human nose, the nose seen as a portion of a human face.
Figure 2:
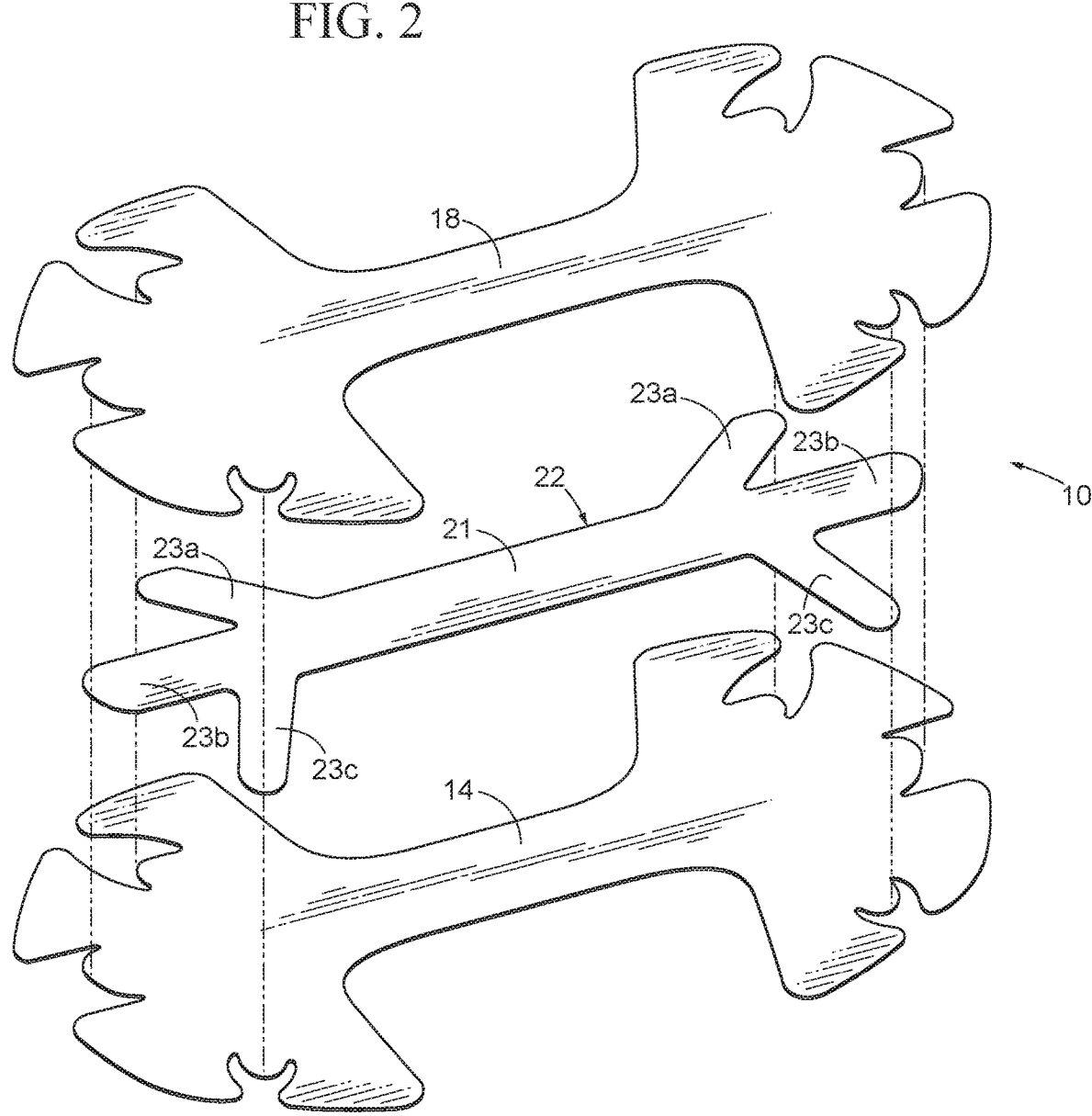
FIG. 2 is an exploded perspective view of the nasal dilator of FIG. 1.

FIG. 1 shows dilator 10 flexed across a human nose, 11, seen as a portion of a human face. FIG. 2 illustrates that dilator 10 comprises a laminate of vertically stacked layers that may include: a base layer comprising at least one base member, 14, a resilient layer comprising at least one resilient member, 22, a cover layer comprising at least one cover member, 18. A protective layer of release liner, not shown, removably covers exposed adhesive from dilator 10 preliminary to application to nose 11.

Figure 3:
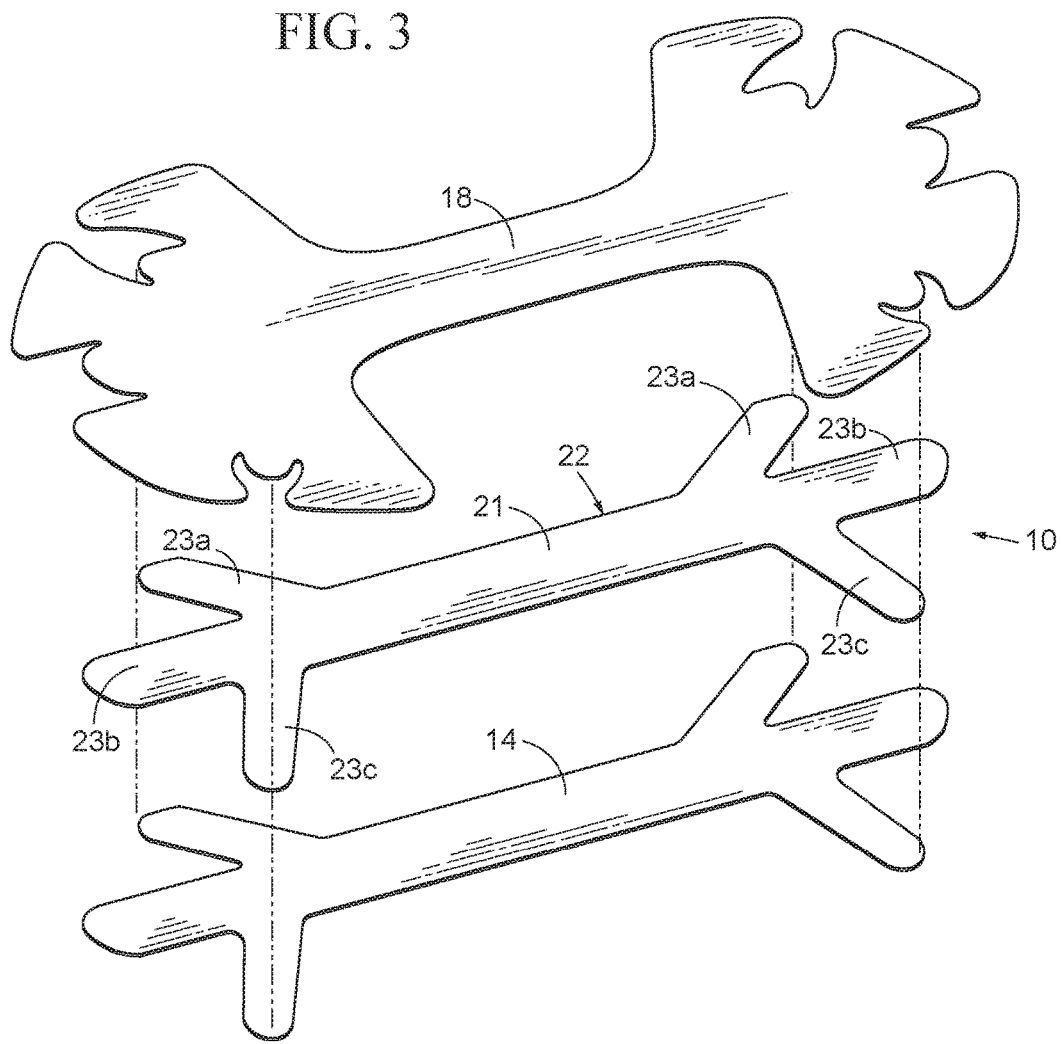
FIG. 3 is an exploded perspective view of a nasal dilator in accordance with the present invention.

The peripheral dimensions of dilator 10 may be defined by the cover layer, the base layer, or a combination thereof. As seen in FIG. 2, for example, the base and cover layers may have the same plan view, or peripheral shape, as each other. Alternatively, as seen in FIG. 3, for example, the base and resilient layers may be identical. In other embodiments, all three layers may have different peripheral shapes.

Figure 4:
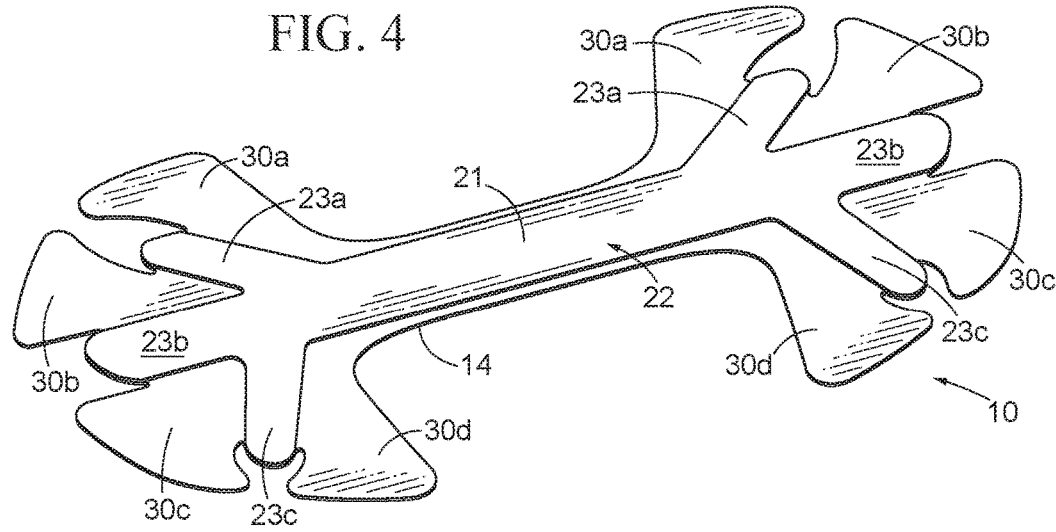
FIG. 4 is a perspective view of a nasal dilator in accordance with the present invention.

Dilator layers may be stacked, or vertically arranged such that the base and cover layers are reversed, or the base layer or cover layer may be eliminated in whole or in part. As seen in FIG. 4, for example, the cover layer is eliminated, so resilient member 22 is uppermost in the stacking order of dilator layers and is exposed and visible when the dilator is engaged on the user's skin.

The preferred materials for the base and cover members may be selected from a range of widely available, preferably medical grade, flexible nonwoven synthetic fabrics or thermoplastic films that are, most preferably, breathable and comfortable on the skin. Any suitable fabric or thermoplastic film, including high Moisture Vapor Transmission Rate (MVTR) polyurethane film, may be used. A pressure sensitive adhesive, preferably biocompatible with external human tissue, may be disposed on at least one flat surface side of the material, in which case a protective, removable, release liner may cover the adhesive to protect it until the user is ready to apply the device.

The at least one resilient member 22 provides resiliency in the form of spring biasing forces as discussed hereinbefore. Resiliency is defined herein as being flexible out-of-plane while remaining substantially rigid in-plane when the dilator is flexed across the bridge of the nose. The preferred material for the resilient member is a thermoplastic resin, which may be selected from a range of thermoplastics having flexural, tensile and elastic moduli so as to have substantial in-plane rigidity and out-of-plane flexibility such that the resilient member has suitable spring biasing properties at a thickness, for example, of from about 0.005" to about 0.015". The most preferred thermoplastic material is a biaxially oriented polyester resin, Poly(ethylene terephthalate) or PET (or boPET). PET is used in a number of medical device applications, is particularly suitable for nasal dilator devices, and is widely available as a medical/industrial commodity.

Figure 5:
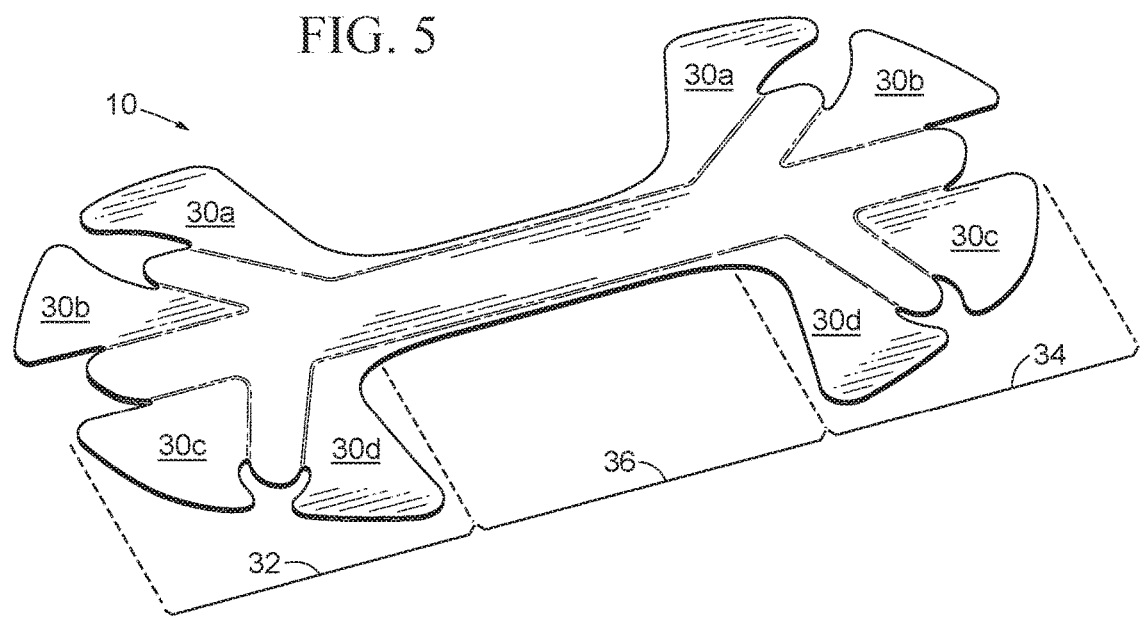
FIG. 5. is a perspective view of a nasal dilator in accordance with the present invention.

The combined layers of dilator 10 form a unitary, or single body, truss. FIG. 5 delineates by brackets and dashed lines the regions of dilator 10, including a first end region, 32, a second end region, 34, and an intermediate region, 36, which separates first end region 32 from second end region 34. Portions of any dilator layer may define a region or a portion thereof, and the layers, members or components of dilator 10 may extend from one region to another. In many embodiments, the width of intermediate region 36 is narrower than the wider end regions 32 and 34, and its length is greater than the length of either end region. In other words, end regions 32 and 34 each represent less than ⅓ of the overall dilator length, and intermediate region 36 represents more than ⅓ of the overall dilator length. End regions 32 and 34 are configured to engage soft tissues associated with the first and second nasal passages, respectively.

Figure 6:
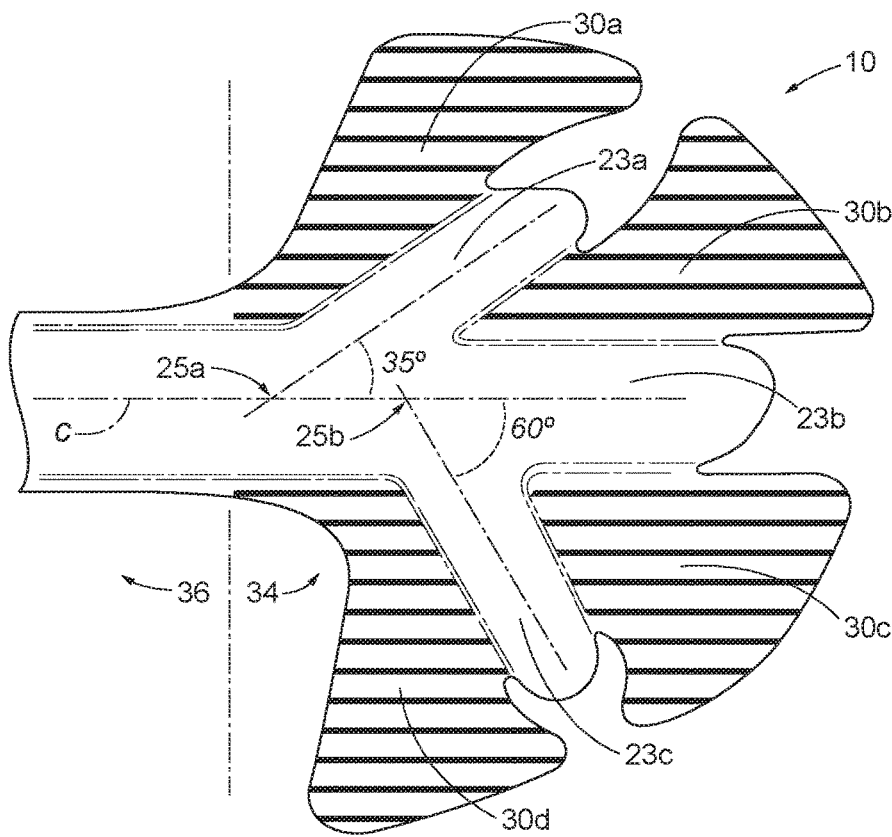
FIG. 6 is a detail view of one end of the dilator of FIG. 5.

Resilient member 22 includes a plurality of spring finger components, 23a, 23b and 23c, extending outward from each end of the resilient member mid-section, 21. These are identified in FIG. 6. Mid-section 2t extends along intermediate region 36 of dilator 10 and has long edges substantially parallel to a longitudinal centerline, c, thereof. Opposing ends of mid-section 21 terminate at or near the boundary separating end region 32 or 34 from intermediate region 36. Thus resilient spring fingers 23 preferably extend entirely within either end region of dilator 10. Spring fingers 23a and 23c, respectively, diverge or branch from longitudinal centerline cat two separation points, 25a and 25b, as seen in FIG. 6. Separation point 25b is positioned further horizontally outward from mid-section 21 than separation point 25a.

Spring fingers 23 extend outward with, and are adjacent to, engagement element tab extensions, 30a, 30b, 30c and 30d. Thick, dark lines in FIG. 6 illustrate the surface area extents of tab extensions 30, each positioned immediately adjacent to one or both sides of each spring finger, such that the spring fingers are interposed therebetween. Tab extensions 30 are part of the engagement element of dilator 10, securing end regions 32 and 34 to nose 11 in the presence of spring biasing forces generated by resilient member 22. The terminal ends of spring fingers 23 are preferably set inward from the tab extension ends, the tab extension ends thus extending beyond the spring finger terminal ends. The tab extension ends may widen so as to extend toward one another without touching, and may extend slightly around the terminal ends of the spring fingers, a short distance therefrom and without touching, such that each tab extension is separate and distinct.

Figure 8:
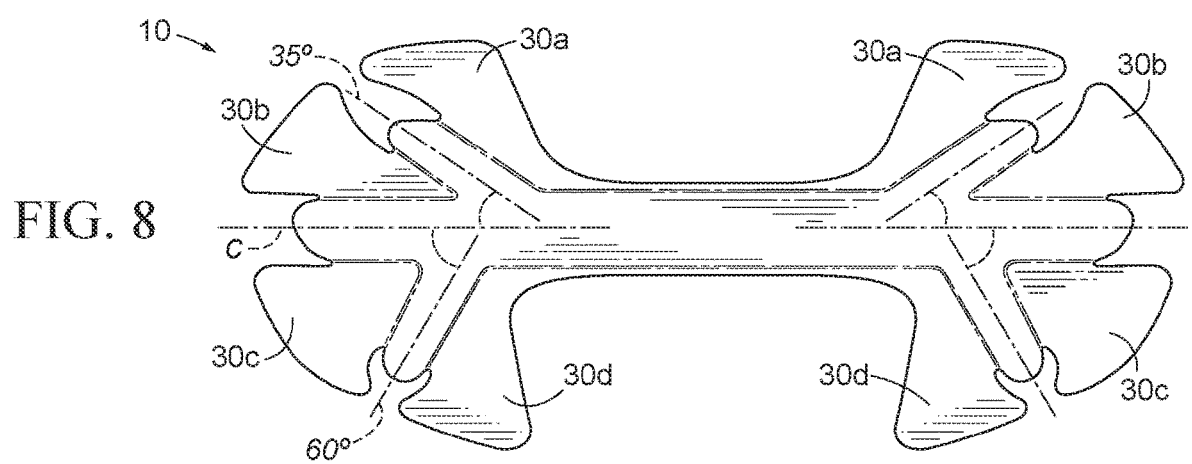
FIG. 8 is a plan view of a nasal dilator in accordance with the present invention.

As depicted in FIGS. 6 and 8, spring fingers 23a and 23c diverge at an angle of about 35 degrees and about 60 degrees, respectively, from longitudinal centerline c. The divergent or branching angle, the positioning of separation points 25a and 25b, and the length of spring fingers 23, combine to direct spring biasing forces to discrete dilation points along the nasal passages of nose 11. Together with the surface area of tab extensions 30, this configuration results in a wider resilient element and a wider end region compared to a nasal dilator having a substantially rectangular resilient element. Greater width together with a total of four tab extensions 30 equates to a greater surface area of end regions 32 and 34, and allows dilator 10 to be more securely engaged to nose 11, compared to a nasal dilator having just two tab extensions positioned one each adjacent and outside a plurality of closely parallel resilient members (as seen, for example, in FIG. 19). Further comparison between nasal dilators of the present invention and prior art nasal dilators may be found hereinbelow, relative to FIGS. 19-22.

Figure 7:
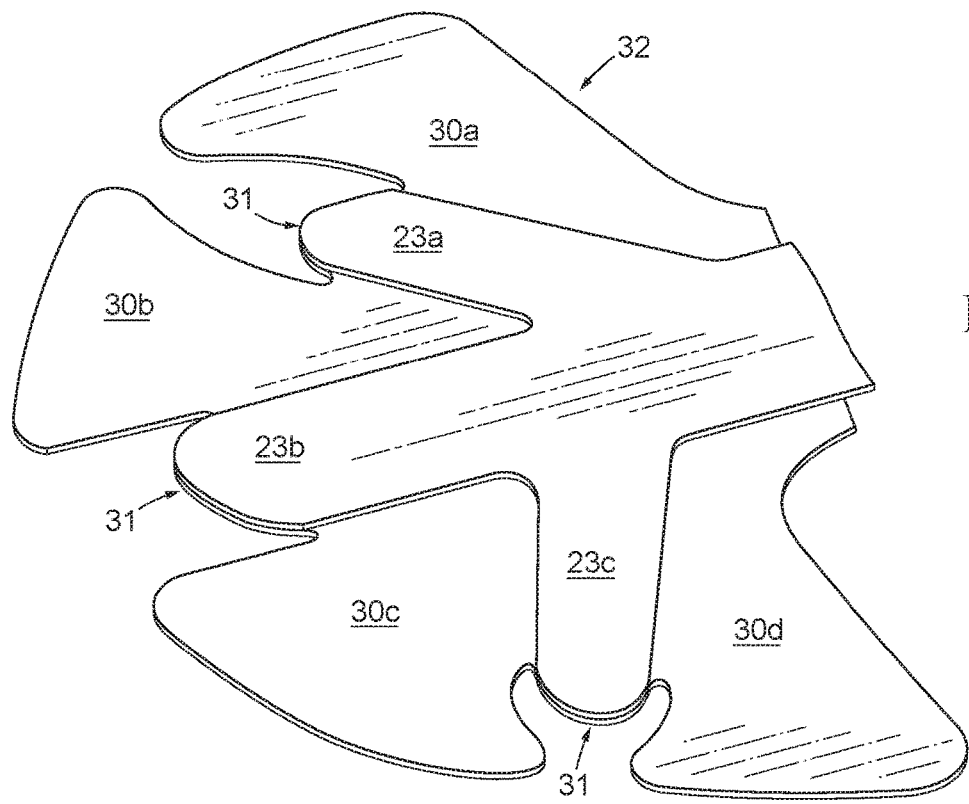
FIG. 7 is a detail view of another end of a dilator of the present invention.

As seen particularly in FIG. 7, the terminal ends of spring fingers 23 are coextensive with and on a common peripheral edge, 31, with portions of the dilator engagement element thereat. (As described hereinbefore, the engagement element may comprise a base layer, cover layer, or both.) Broken lines in the exploded perspective views of FIGS. 2, 3, and 14 also indicate the common peripheral edge alignment of spring finger terminal ends to the engagement element of dilator 10.

Figure 9:
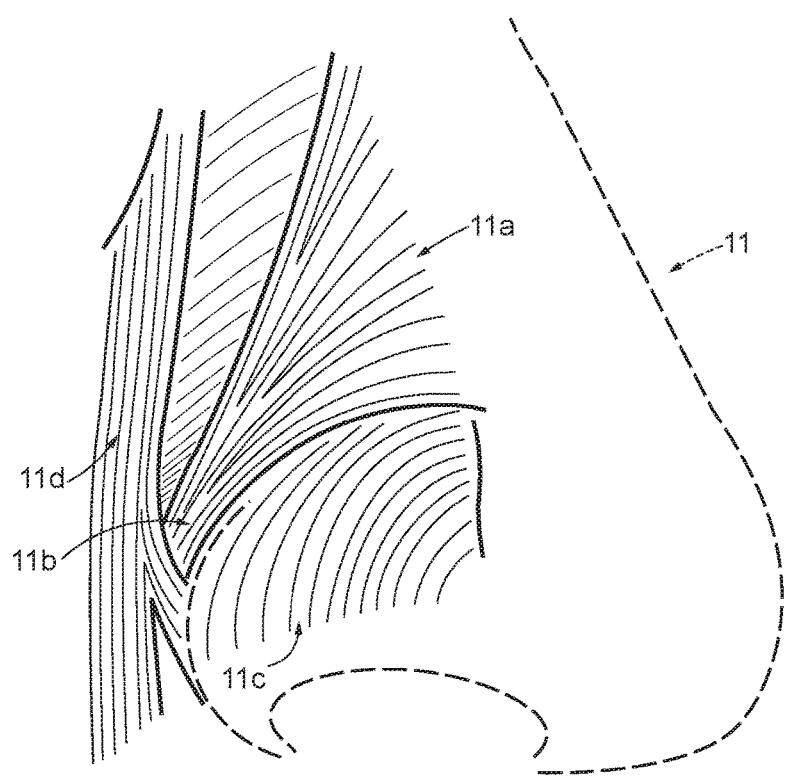
FIG. 9 is a perspective view of a human nose showing several muscles thereabout.
Figure 10:
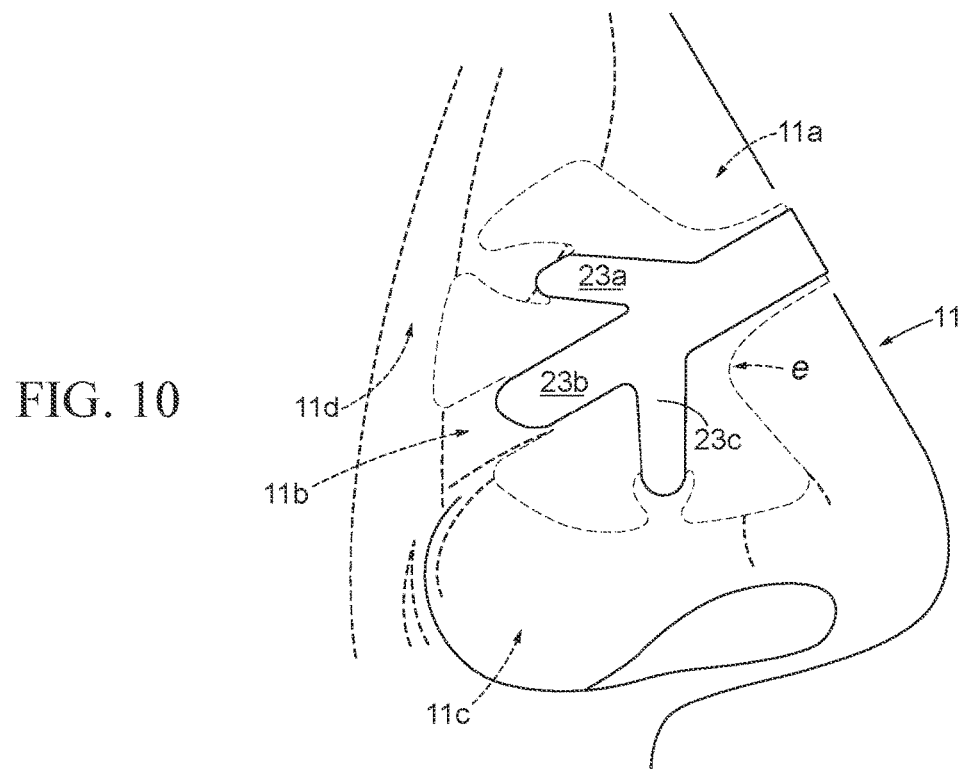
FIG. 10 is a perspective view of a human nose showing positioning of the nasal dilator of FIG. 1 relative to the several muscles thereabout.
Figure 11:
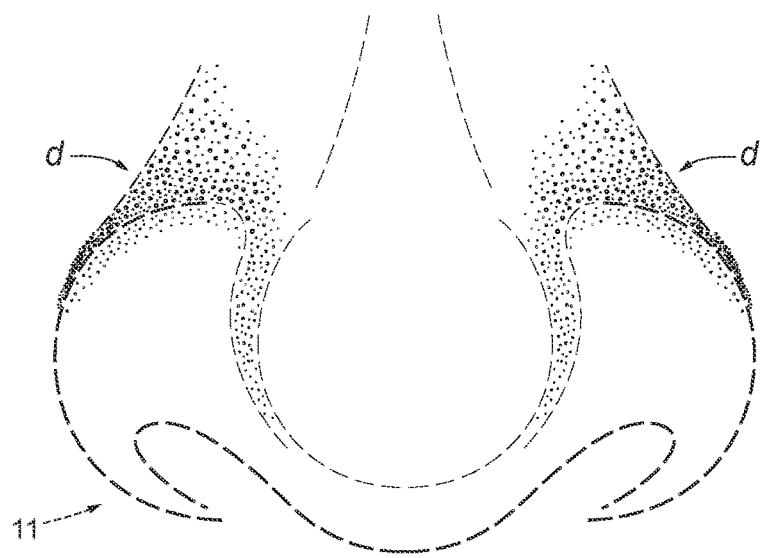
FIG. 11 is a frontal view of the human nose showing by stippling an anatomical depression, or valley, adjacent each nostril thereof.

The total resiliency, or spring biasing forces, distributed by dilator 10 extend through mid-section 21 and spring fingers 23 to multiple discrete dilation points along the first and second nasal passages, as described hereinbefore. These dilation points are associated with several muscles about nose 11, as shown in FIGS. 9 and 10: the transverse portion of the nasalis muscle, 11a, the alar portion of the nasalis muscle, 11b, the dilator naris anterior muscle, 11c, and the levator labii superioris muscle, 11d. It is held that *"The dilator naris muscle, the nasalis muscle and the apicis nasi muscle are strongly related to respiration, contributing to the prevention of collapse of the nasal valve."* (Bruintjes T D, Van Olphen A F, Hillen B, Weijs W A. Electromyography of the human nasal muscles. *Eur Arch Otorbinolaryngol* 1996; 253:464-469.)

As more particularly seen in FIG. 10, spring finger 23C extends downward from the nasal valve area along a portion of naris muscle 11C; spring finger 23a extends up and away from the nasal valve area across a portion of transverse nasalis muscle 11a; and spring finger 23b extends substantially over and along the nasal valve along alar nasalis muscle 11b. Spring fingers 23 and tab extensions 30 extend, or direct, stabilization and dilation to this greater portion of the nasal passages compared to a nasal dilator in which a substantially rectangular resilient member(s) overlays only the tissues over the nasal valve.

The engagement element, e, of dilator 10 may be depicted by shadow lines, as seen in FIGS. 10, 12, and 13-18. Engagement element e may comprise a layer or any combination of layers that make up the engagement element of dilator to as described herein. The dilator engagement element is referenced generically in this manner to avoid repeating the several stacking orders of dilator layers previously discussed with respect to FIGS. 2-4.

An anatomical depression, or valley, d, adjacent each nostril of nose 11 is shown by stippling in FIGS. 1, 11-12, 16 and 18. Valley d is roughly triangular in shape; bounded from top to bottom by the vertical alar groove, the supra alar groove and alar facial crease (or groove). The triangular base, on top, has the shallowest depression, and the tip of the triangle, at the bottom, has the deepest.

Figure 12:
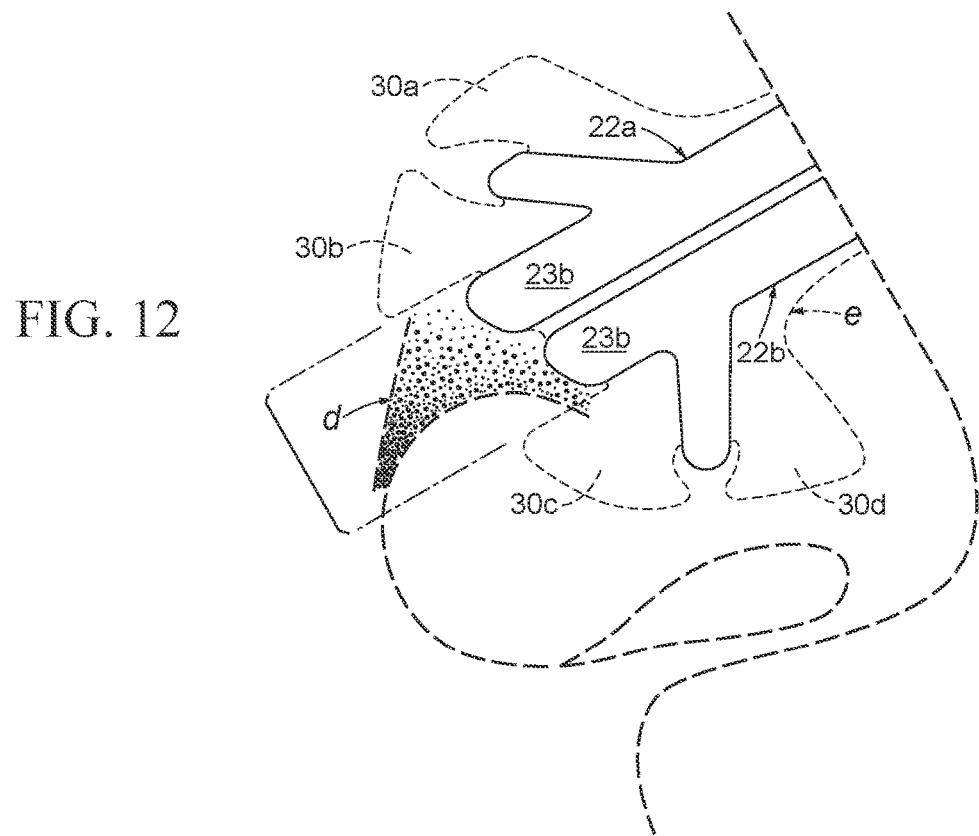
FIG. 12 is a perspective view of a nasal dilator in accordance with the present invention flexed across a human nose.

It will be apparent to one of ordinary skill in the art that where a portion of nasal dilator surface area extends across or spans the anatomical depression, the nasal dilator will thus be non-engaged to the skin surface thereat. Areas of non-engagement can lead to the nasal dilator having a greater propensity to prematurely disengage, or peel, from the nose during use. Accordingly, the end regions of dilator 10 are configured to extend around, and particularly, to avoid extending across, or spanning, valley d, so as to maximize skin surface contact of dilator 10 to nose 11. FIG. 12 particularly illustrates by a bracket and broken lines that valley d is thus bordered by inside long edges of tab extensions 30b and 30c and a portion of the lateral end edge of dilator to corresponding to terminal ends of spring fingers 23b.

Figure 13:
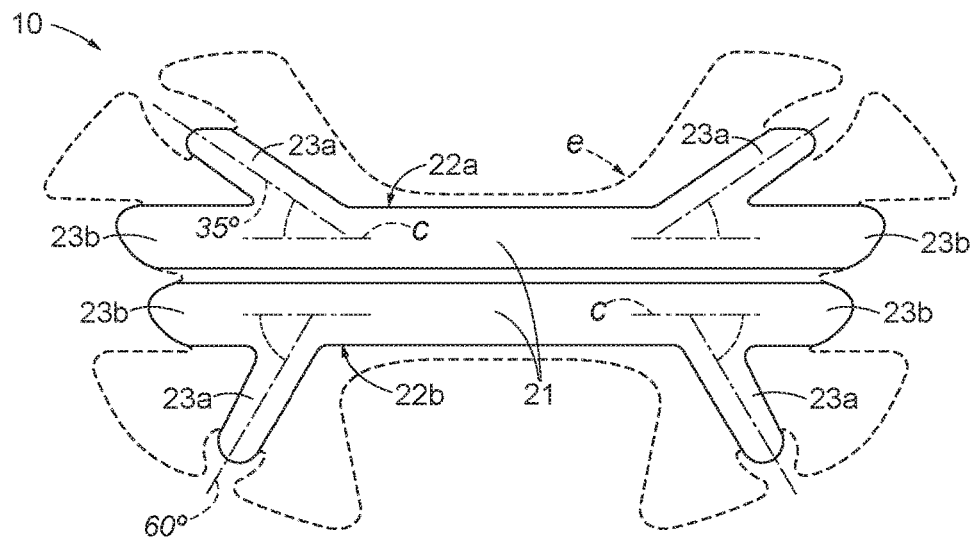
FIG. 13 is a plan view of the nasal dilator of FIG. 12.

The resilient layer of dilator 10 may be bisected lengthwise into two parts, as described hereinbefore, to form separate resilient members 22a and 22b, as seen in FIGS. 12 and 13. Each resilient member has two spring fingers 23a and 23b extending from each end of mid-section 21. Thus each end region of dilator 10 includes four spring fingers and four tab extensions. Spring fingers 23a diverge obliquely, while spring fingers 23b are substantially parallel to longitudinal centerline c. As described hereinbefore, resilient spring fingers 23 are preferably confined within each end region of dilator to.

Figure 14:
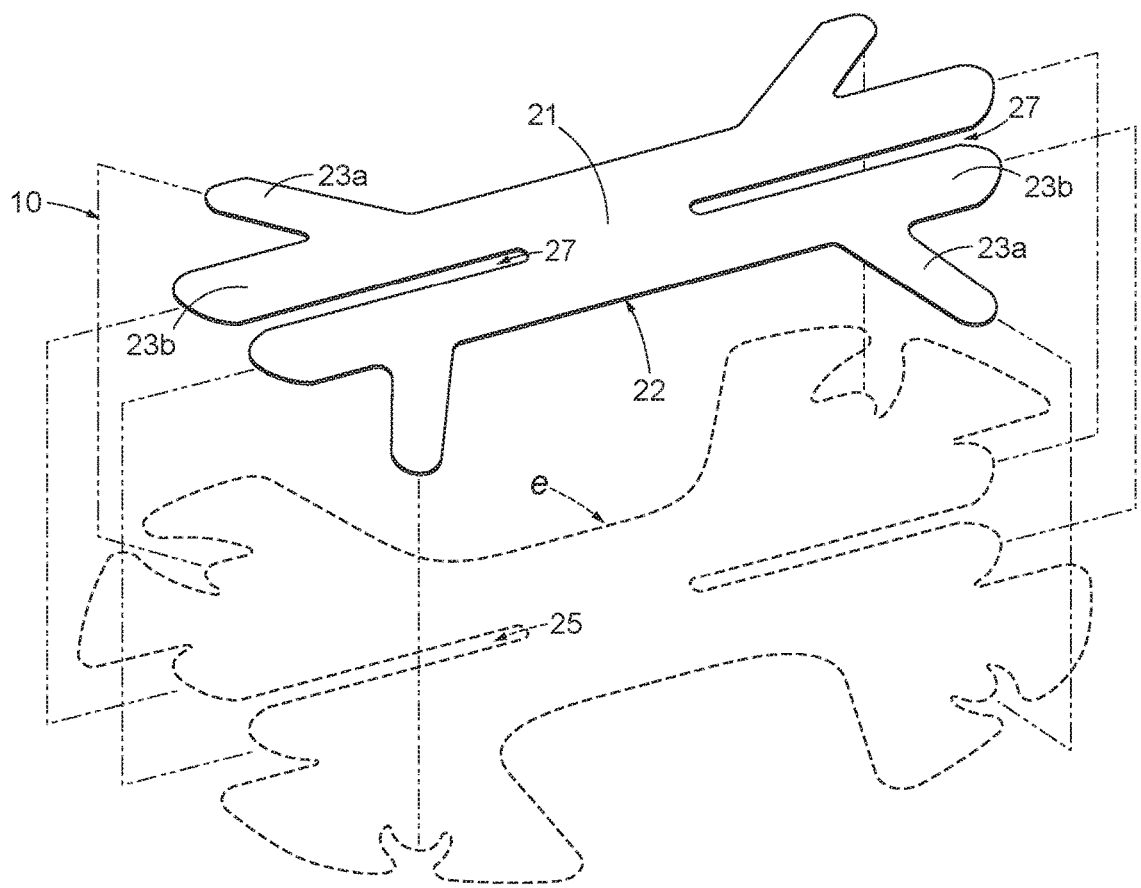
FIG. 14 is an exploded perspective view of a nasal dilator similar to that shown in FIGS. 11 and 12.

In lieu of being bisected lengthwise into two parts, a single resilient member 22 may be slotted to form four resilient branches. FIG. 14 shows a slot, 27, extending inward from at least one resilient member lateral end edge. Slot 27 may extend to, short of, or beyond, the boundary between either end region 32, 34 and intermediate region 36 of dilator to. As shown, slot 27 extends into mid-section 21, past said boundary. Slot 27 may be formed coextensively in both resilient member 22 and at least one layer of the engagement element. Alternatively, slot 27 may be formed in just the resilient member (not shown). Each resilient branch formed by slot 27 includes two spring fingers 23a and 23b. Otherwise, end regions 32 and 34 may retain substantially the same configuration of tab extensions and spring fingers as seen in FIGS. 12 and 13. It should be apparent to those of ordinary skill in the art that slot 27 may alternatively take the form of a slit, for example, or an elongated notch or other opening or material separation.

Figure 15:
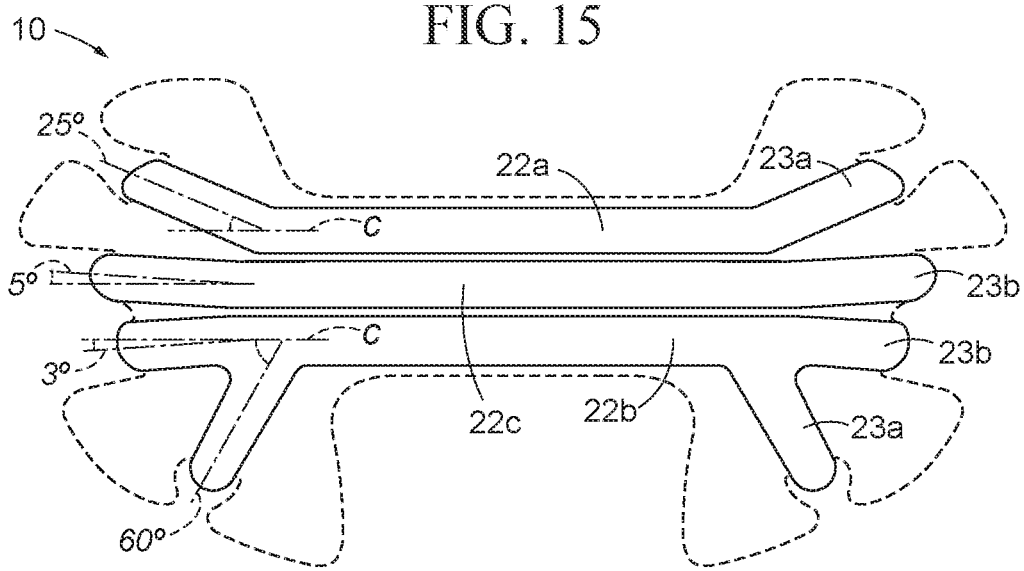
FIG. 15 is a plan view of a nasal dilator in accordance with the present invention.
Figure 16:
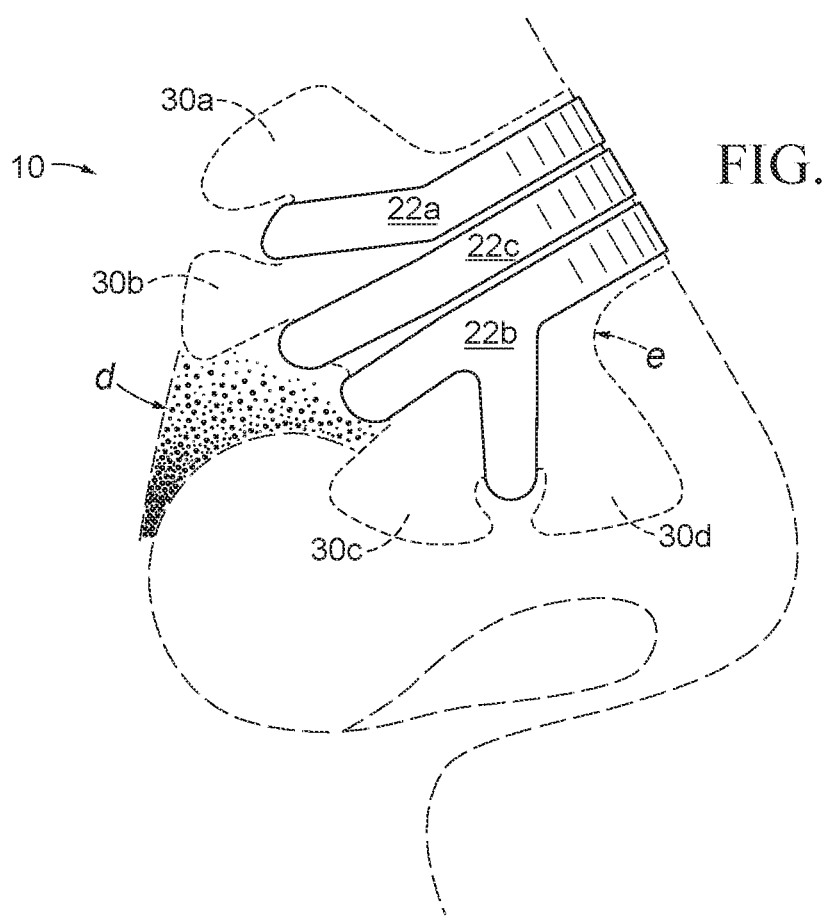
FIG. 16 is a perspective view of the nasal dilator of FIG. 15 engaged to a human nose.

The resilient layer of dilator 10 may be trisected lengthwise into three separate resilient members, 22a, 22b and 22c, as illustrated in FIGS. 15 and 16. Resilient members 22a and 22c have a single spring finger, 23a and 23b, respectively, extending from each end of mid-section 21. Resilient member 22b has two spring fingers, 23a and 23b, diverging from each end of mid-section 21. FIG. 15 further illustrates that, from top to bottom, spring fingers 23a diverge obliquely about 25 degrees and about 60 degrees, respectively, from a centerline c; spring fingers 23b diverge slightly from centerline c, about 5 degrees and 3 degrees, respectively. The slight divergence of spring fingers 23b creates more space for extending tab extensions 30b and 30c around valley d.

Figure 17:
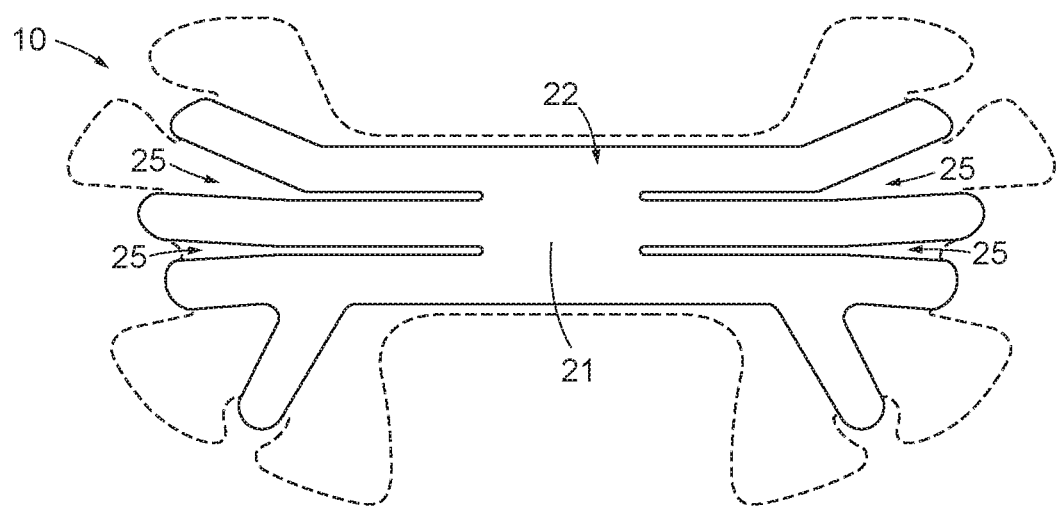
FIG. 17 is a plan view of a nasal dilator in accordance with the present invention.
Figure 18:
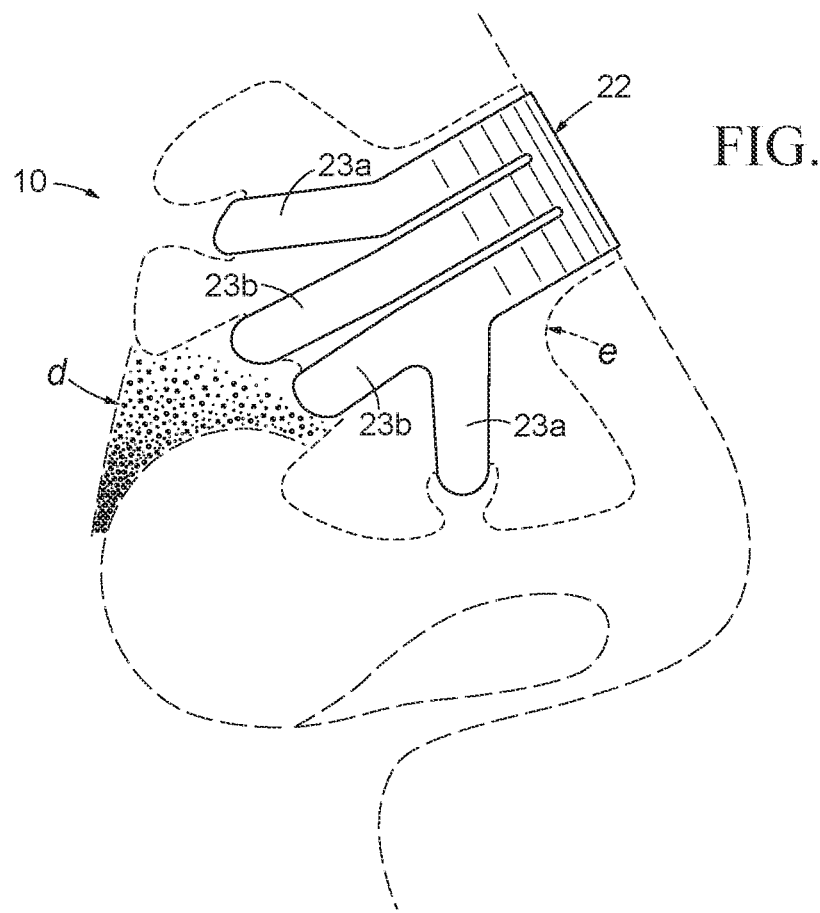
FIG. 18 is a perspective view of the nasal dilator of FIG. 17 engaged to a human nose.

A single resilient member 22 may be notched and/or slotted to form six resilient branches extending outward from the center of mid-section 21, as seen in FIGS. 17 and 18. Slots 27 comprise both an elongated notch and a slot, and may extend to, short of, or beyond, the boundary between either end region and intermediate region 36 of dilator to. FIGS. 17 and 18 show slots 27 extending into mid-section 21, past the separating boundary. Slot 27 may be formed coextensively in both resilient member 22 and at least one layer of the engagement element. Alternatively, slot 27 may be formed in just the resilient member. A resilient branch may include spring fingers, or may include divergent end portions. As shown, resilient member 22 is slotted to form a similar end region configuration as that depicted in the embodiment of FIGS. 15 and 16.

Bisecting or slotting the resilient element allows dilator 10 to have greater overall axial/torsional flexibility about its longitudinal centerline. Greater flexibility allows dilator 10 to better conform to contours of the nose and to better balance spring biasing forces between tab extensions 30a/30b and 30c/30d, respectively, on each side of the centerline.

Additionally, a slotted resilient member 22 forms a contiguous area extending between the long edges at the center of mid-section 21. The contiguous area may generate greater spring biasing forces thereat compared to a bisected/trisected resilient layer.

FIGS. 19-22 compare overall dimensions and aspect ratios of prevalent prior art nasal dilators to that of nasal dilators of the present invention. As noted hereinbefore, nasal dilators of the present invention are drawn to scale. The prior art nasal dilators depicted in FIG. 19, being widely available to the public and thus physically measurable, are also drawn to scale. Both the prior art nasal dilators and nasal dilators of the present invention are drawn to size relative to each other.

As shown in FIG. 19, the prior art nasal dilators have two or three closely adjacent parallel resilient bands and four tab extensions, x, at each of four corners thereof. External nasal dilators having this configuration account for the vast majority of all external nasal dilators sold in the U.S. consumer market since 1995, as may be found, for example, in data from the Nielsen Company, US, LLC retail measurement services. The three-band nasal dilator is disclosed in U.S. Pub. No. 20110000483, and the two-band nasal dilator is disclosed in U.S. U.S. Pat. No. 5,533,503.

These prior art nasal dilators have very similar resiliency to that of dilator 10: U.S. Pub. No. 20110000483 teaches that "The total spring force delivered by the resilient element as a whole should be from about 15 grams (gm) to about 60 gm. In one embodiment, the total spring force delivered by the resilient element as a whole should be from 25 gm to about 35 gm." U.S. Pat. No. 5,533,503 teaches that "A desired functional range of dilating force (i.e., the spring biasing force due to the resiliency of the resilient means of the nasal dilator) is typically in the range of 5 to 50 grams . . . The nasal dilator 10, of the present invention, is constructed to produce from 20 to 30 grams of dilating spring biasing force . . . " (Additionally, U.S. Pat. No. 5,533,503 provides dimensions for its two resilient members: "The first and second resilient hands 30a and 30b are each formed of a plastic material . . . that is approximately 0.080" to 0.135" wide and 0.010" thick.") The range of spring biasing force delivered by nasal dilators of the present invention, as described herein, is substantially the same as the prior art nasal dilators.

Nasal dilators of the present invention apply spring biasing forces to a greater area of the nasal passages, and withstand the same or greater spring biasing forces compared to the prior art nasal dilators, due to greater end region width and greater surface area formed by the configuration of spring fingers 23 and tab extensions 30. The prior art dilators include upper and lower tab extensions x one to each outermost side of either two or three parallel adjacent resilient members. By comparison, nasal dilators of the present invention have three or four spring fingers interposed between four tab extensions at each end region.

A standard unit of measure (1.0) is used in FIGS. 19-22 to compare length and width dimensions of the nasal dilators to each other: overall width, o, (o=1.0) resilient element width, w, (w=1.0) and overall length, l(l=1.0). Comparative values are shown in the table at FIG. 23.

It may be apparent to those of ordinary skill in the art that, since the length of an external nasal dilator generally spans the width of the average human adult nose from nostril to nostril, there is relatively little difference in the l dimension between the prior art nasal dilators and nasal dilators of the present invention; that difference is less than 10%. However, there are significant differences in the o and w dimensions between dilator 10 and the prior art nasal dilators. For example, dilator 10 of FIG. 21 has a 73% greater overall width compared to the overall width of the prior art two-band nasal dilator, and its resilient element width is 110% greater compared to the resilient element width of the prior art two-band nasal dilator.

Figure 21:
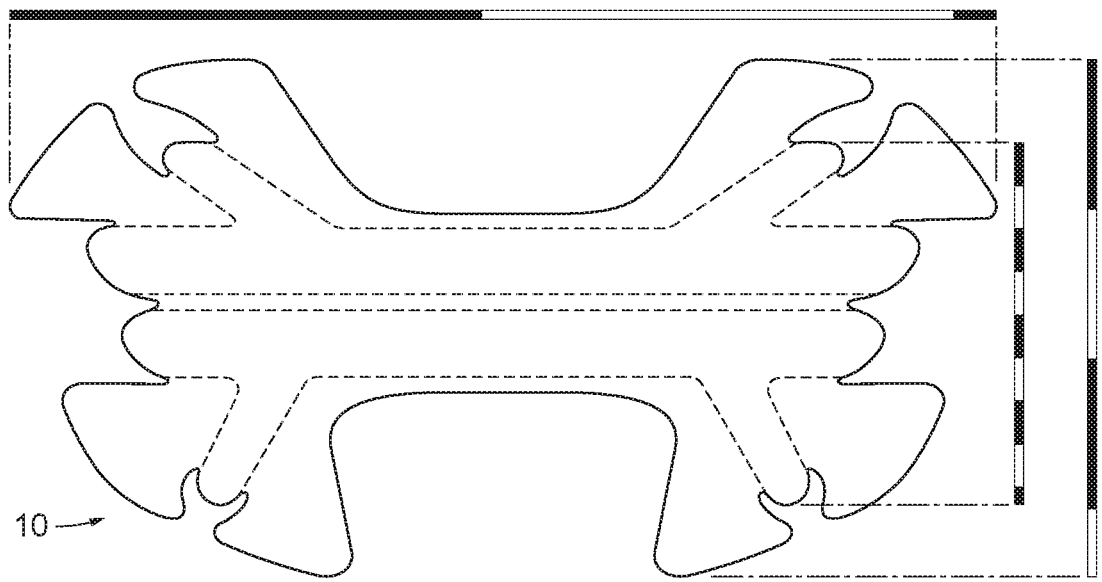
FIG. 21 is a plan view of the nasal dilator of FIG. 13.
Figure 22:
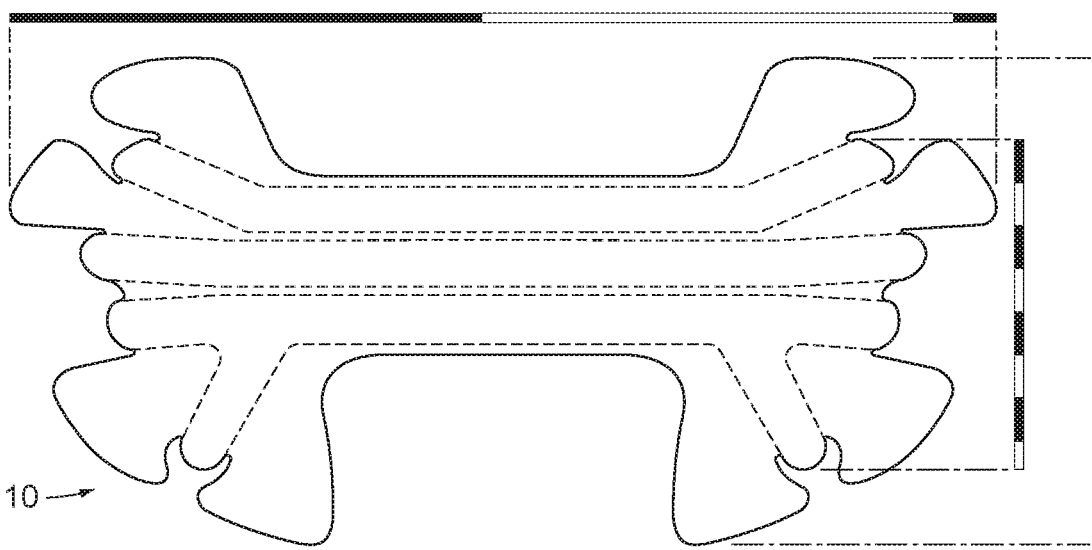
FIG. 22 is a plan view of the nasal dilator of FIG. 15.

Thus there are significant differences in aspect ratios l:o and l:w between the prior art nasal dilators and nasal dilators of the present invention, as detailed in the table and charts below. (For this purpose, width dimensions o and w are expressed as 1; overall length l is expressed as a multiple thereof.) For example, the ratio of overall length to overall width of the prior art two-band nasal dilator is 3.42:1, and its ratio of overall length to resilient element width is 7.44:1. That is, the overall length of the prior art two-band nasal dilator is 3.42 times greater than its overall width, and is 7.44 times greater than its resilient element width:

|  | ASPECT RATIO (l:o) | ASPECT RATIO (l:w) |
|---|---|---|
| PRIOR ART TWO-BAND | 342:1 | 7.44:1 |
| PRIOR ART THREE-BAND | 2.70:1 | 5.46:1 |
| DILATOR 10, FIG. 20 | 2.30:1 | 3.59:1 |
| DILATOR 10, FIG. 21 | 1.91:1 | 2.72:1 |
| DILATOR 10, FIG. 22 | 2.03:1 | 2.98:1 |

Nasal dilators of the present invention have an aspect ratio of overall length to overall width (l:o) that is somewhat lesser than that of the prior art nasal dilators, as more particularly illustrated in the first chart at FIG. 24, 2401.

Furthermore, the aspect ratios of overall length to resilient element width (l:w) is considerably lesser in nasal dilators of the present invention compared to the prior art nasal dilators, as shown in the second chart at FIG. 24, 2402.

Accordingly, nasal dilators of the present invention have a preferred aspect ratio of overall length to overall width (l:o) in a range of from about 1.80-2.50 to 1, wherein the ho aspect ratios of the prior art nasal dilators are outside this range, being from 2.70-3.42 to 1.

Additionally, the preferred aspect ratio of overall length to resilient element width (l:w) of dilator 10 is in a range of from about 2.50-3.80 to 1, wherein the l:w aspect ratios of the prior art nasal dilators are well outside this range, being from 50.46-70.44 to 1.

As illustrated and described in examples of the preferred embodiments, the present invention provides novel and non-obvious articles for dilating external tissue, particularly in the form of external nasal dilator devices.

I claim:

1. A nasal dilator comprising:
   an engagement element comprising at least one engagement layer having a peripheral edge, the peripheral edge defining an intermediate region and opposing end regions including tab extensions thereof, the intermediate region having a greater length than either end region;
   a resilient element capable of providing spring biasing forces, the resilient element comprising at least one mid-section and a plurality of spring fingers extending horizontally outward from each end of the at least one mid-section, the plurality of spring fingers numbering at least three spring fingers;
   wherein the at least three spring fingers are interposed between four separate and distinct tab extensions;

wherein terminal ends of the spring fingers terminate along portions of the at least one engagement layer peripheral edge;

wherein the resilient element is bilaterally symmetric; and wherein a first centerline of a first spring finger intersects a second centerline of a second spring finger at an intersection point, said intersection point lying in a lateral-most one-fourth to one-third of the resilient element.

2. The nasal dilator of claim 1, wherein the at least one engagement layer is selected from the group consisting of:
   a) a base member;
   b) a cover member; or
   c) a base member and a cover member.

3. The nasal dilator of claim 1 wherein at least some of the spring fingers diverge obliquely from a longitudinal centerline of the nasal dilator, such that when the nasal dilator is in use on a nose of a user at least one of an upper spring finger extends up and away from the nasal valve area, at least one of a middle spring finger extends substantially over and along the nasal valve, and at least one of a lower spring finger extends away and downward from the nasal valve area toward the nostril opening.

4. The nasal dilator of claim 1 wherein when the nasal dilator is in use on a nose of a user, a spring finger overlays and extends along an alar nasalis muscle of the nose, another spring finger overlays and extends across a portion of a transverse nasalis muscle of the nose, and another spring finger overlays and extends along a portion of a naris muscle of the nose; and wherein said muscles are strongly related to respiration and contribute to the prevention of collapse of the nasal valve, said muscles being supported by at least a portion of each of said spring fingers.

5. The nasal dilator of claim 1 wherein an aspect ratio computed as length (l) to overall width (o), l:o, is less than 2.70:1.

6. The nasal dilator of claim 1 wherein an aspect ratio of dilator overall length to dilator overall width is in a range between 1.8 and 2.5 to 1; and wherein an aspect ratio of dilator overall length to resilient element width is in a range between 2.5 and 3.8 to 1.

7. The nasal dilator of claim 1 wherein the plurality of spring fingers extending horizontally outward is four; and wherein the four separate and distinct tab extensions are arranged such that upper and lower spring fingers have a tab extension adjacent each of two long edges, and two middle spring fingers have adjacent inside long edges absent a tab extension therebetween, a tab extension being adjacent each outside long edge thereof.

8. The nasal dilator of claim 1, wherein the resilient element is split lengthwise from end to end substantially parallel to a longitudinal centerline thereof so as form two or three separate resilient members.

9. The nasal dilator of claim 1, wherein the resilient element comprises a single resilient member slotted inwardly from at least one lateral end edge thereof so as to form two or three resilient branches extending from the resilient member mid-section into at least one end region.

10. The external nasal dilator of claim 9 wherein a centerline of a first spring finger intersects a centerline of a third spring finger, a second spring finger lying in the lateral-most one-fourth of the branched resilient member.

11. The nasal dilator of claim 1, wherein when the nasal dilator is in use on the nose of the user the opposing end regions extend around an anatomical depression adjacent each nostril of the nose, such that no portion of the nasal dilator spans the anatomical depression; and wherein the anatomical depression is defined by a vertical alar groove, a supra alar groove and an alar facial groove.

* * * * *